Sept. 18, 1934. C. MALLERIN Plant Pat. 103
ROSE
Filed May 5, 1934
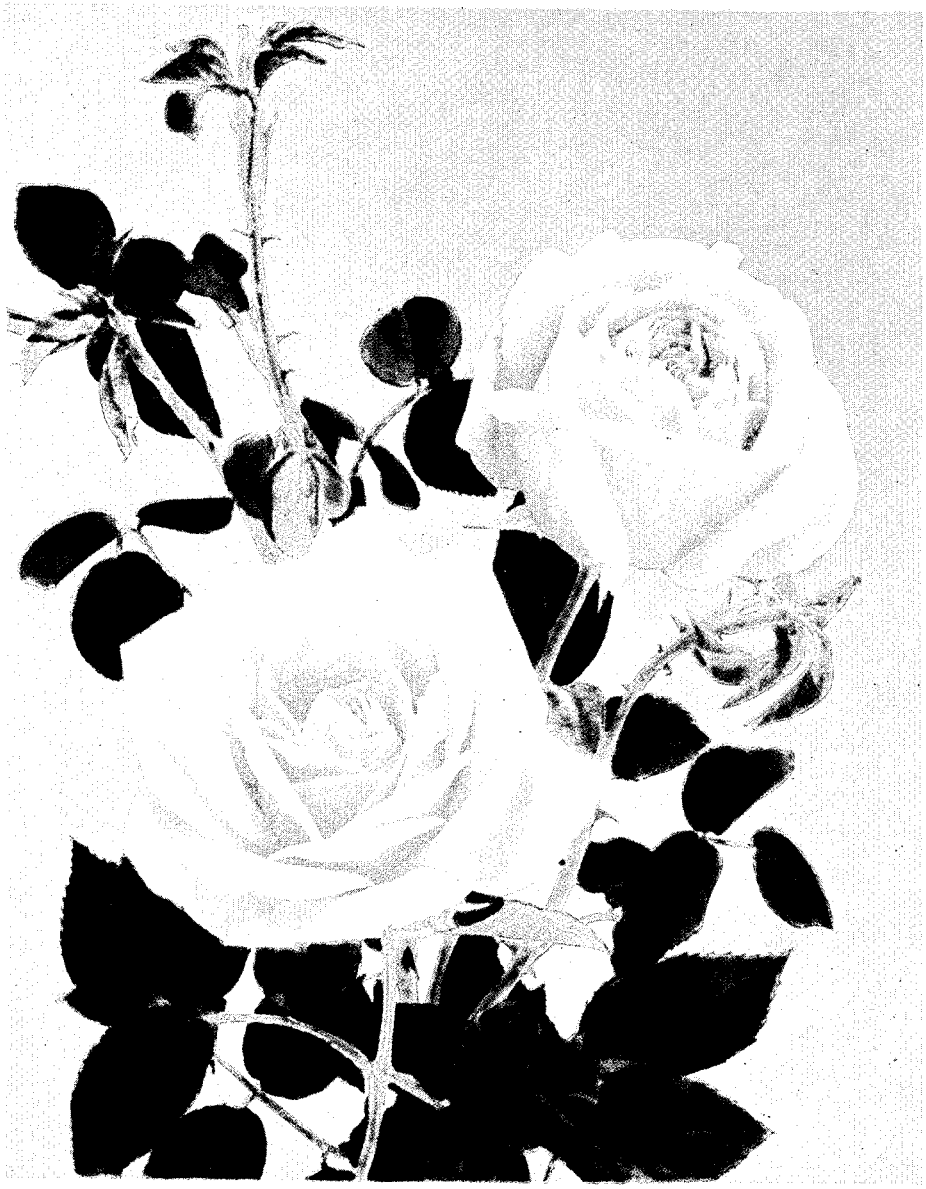
Inventor
Charles Mallerin
By Robb & Robb
M. D. Macdonald
Attorneys Patented Sept. 18, 1934

Plant Pat. 103

UNITED STATES PATENT OFFICE

103

ROSE

Charles Mallerin, Varces, France, assignor to The Conard-Pyle Company, West Grove, Pa.

Application May 5, 1934, Serial No. 724,156

1 Claim. (Cl. 47—61)

This invention relates to a new variety of rose, the result of definite breeding in an effort to produce a better yellow rose for garden purposes.

This new rose was produced by crossing the Pernetiana Hybrid Rose, "Julien Potin" and the Pernetiana Hybrid Rose, "Margaret McGredy"; Julien Potin was used as the female, or seed parent, and Margaret McGredy as the male, or pollen parent.

This new rose has not only inherited the best characters of both parents, but has more beautiful flowers and produces more of them than either parent.

The plant of this new rose makes better growth, has more and more persistent foliage than any yellow rose that I am familiar with. This new variety has been asexually propagated and is found to reproduce true to form.

The following is a detailed description of this rose plant and its flower, it being understood that slight variations from the named characteristics take place due to environment or season. The coloring of the flower is slightly different according to the season of blooming as hereinafter referred to. The coloring in the drawing filed herewith is that found in the autumnal season and all references to colors herein are based upon Royal Horticultural Society's Color Chart.

Parentage.—
Seedling.
*Seed parent.*—Julien Potin.
*Pollen parent.*—Margaret McGredy.
Classification.—
Pernetiana Hybrid, usually commercially classed as Hybrid tea.

*Flower*

Blooming habit.—
*Recurrent.*—Almost continuous.
Bud.—
*Size.*—Medium.
*Form.*—Ovoid.
*Color.*—Summer buds pale yellow with carmine stains. Autumn buds creamy orange with heavy carmine markings.
*Sepals.*—Smooth at base, feathery at ends, curl back as bloom opens.
*Calyx.*—Medium size, goblet shaped, smooth.
*Peduncle.*—Long, bronzy green, bristly, heavy.
*Opening.*—Opens well, very little affected by weather.
Bloom.—
*Size.*—Large 3½ to 4 inches when fully open.
*Borne.*—Singly.
*Stems.*—Medium length, strong.
*Form.*—High centered bloom, slightly cupped when fully open.
*Permanence.*—Long lasting.
*Petalage.*—Very double, 80 to 100 petals.
*Color.*—Deep golden yellow, except at edges of petals, which are pale lemon yellow with a slight pink flush.
*Discoloration.*—Becomes a lighter yellow but does not turn white.
*Texture.*—Medium, neither leathery nor tissue like.
*Appearance.*—Satiny finish, both inside and out.
*Form.*—Ovoid.
*Arrangement.*—Imbricated, quantity of short petals and petaloids in center.
*Persistence.*—Drop off cleanly.
*Fragrance.*—Strong.
*Nature.*—Fruity.
*Lastingness.*—Still strong after plants are full blown.
Genital organs.—
*Stamens, anthers.*—Medium size, average number; color, yellow; arrangement, regular around edge of calyx.
*Stamens, filaments (threads).*—Medium length; color, red.
Color.—
*Pollen.*—Orange.
*Styles.*—Bunched, uneven length, slender.
*Stigmas.*—White.
*Ovaries.*—All enclosed in calyx.
Fruit.—
*Form.*—Pear shaped, slightly bent at stem. Bears very few fruits.
*Aspect.*—Smooth.
*Sepals.*—Permanent, long, sometimes straight, sometimes recurved.

*Plant*

Form.—
Bush.
Growth.—
Vigorous, branching.
Foliage.—
Five and seven leaflets.
*Size.*—Medium.
*Quantity.*—Abundant.
*Color.*—New foliage: Upper side light green; under side pale green. Old foliage: Upper side dark green; under side light green.
*Shape.*—Oval, pointed.
*Texture.*—Upper side, leathery glossy; underside, rough. Ribs and veins ordinary, regular.
*Edge.*—Serrated.

*Serration.*—Regular, shallow indentations.
*Leaf stem.*—Green. Under side prickles.
*Stipules.*—Medium, smooth, ending in fine points.
*Disease resistance.*—Resistant.
Wood.—
*New wood.*—Color, pale bronzy green, bark smooth.
*Old wood.*—Color, light green, bark smooth.
Thorns.—
*Quantity.*—Average.
*Form.*—Broad base, medium length, hooked.
*Color when young.*—Red.
*Position.*—Irregular.
*Prickles.*—None.
*Short needles.*—None.

I claim:

The new variety of rose, characterized by the unusual combination of gold, lemon, and pink in the large double bloom, and the vigorous growth, persistent foliage, and exceptional producing powers of the plant, as shown and described.

CHARLES MALLERIN.